(12) United States Patent
Tengler

(10) Patent No.: US 12,037,620 B2
(45) Date of Patent: *Jul. 16, 2024

(54) CANNABINOID AND TERPENE PRESERVATION IN BIOMASS USING WHOLE FERMENTATION BROTH

(71) Applicant: Van Grow LLC, Longmont, CO (US)

(72) Inventor: Robert Tengler, Longmont, CO (US)

(73) Assignee: Van Grow, LLC, Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,385

(22) Filed: Aug. 19, 2022

(65) Prior Publication Data

US 2022/0411827 A1 Dec. 29, 2022

Related U.S. Application Data

(63) Continuation of application No. 17/013,004, filed on Sep. 4, 2020, now Pat. No. 11,453,894.

(60) Provisional application No. 62/895,874, filed on Sep. 4, 2019.

(51) Int. Cl.
*C12P 1/04* (2006.01)
*C12N 1/20* (2006.01)

(52) U.S. Cl.
CPC . *C12P 1/04* (2013.01); *C12N 1/20* (2013.01)

(58) Field of Classification Search
None
See application file for complete search history.

(56) References Cited

U.S. PATENT DOCUMENTS

| | | |
|---|---|---|
| 9,908,832 B2 | 3/2018 | Leker et al. |
| 10,982,243 B2 | 4/2021 | Butt et al. |
| 10,988,785 B1 | 4/2021 | Butt et al. |
| 2022/0411827 A1* | 12/2022 | Tengler .............. A01N 3/00 |

* cited by examiner

*Primary Examiner* — Hope A Robinson
(74) *Attorney, Agent, or Firm* — Edwin S. Flores; Daniel J. Chalker; Chalker Flores, LLP

(57) ABSTRACT

The present invention includes a method of preserving cannabinoid concentration in a biomass comprising: providing a hemp biomass in an aqueous solution; adding a culture of a cannabinoid preserving *Bacillus* bacteria to the hemp biomass solution; and culturing the hemp biomass with the *Bacillus* bacteria under conditions in which the cannabinoid concentration is maintained.

7 Claims, 1 Drawing Sheet

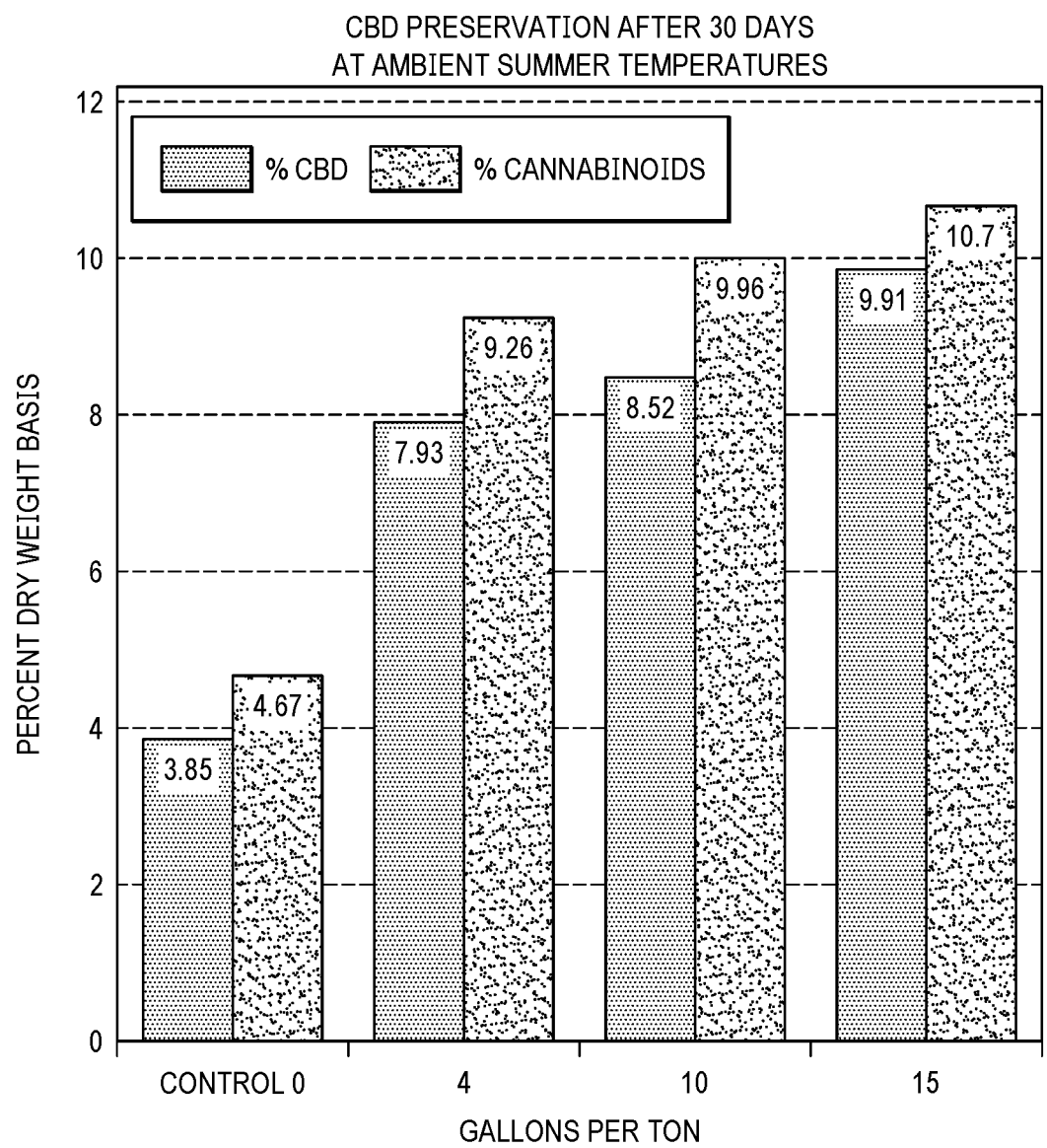

CANNABINOID AND TERPENE PRESERVATION IN BIOMASS USING WHOLE FERMENTATION BROTH

CROSS-REFERENCE TO RELATED APPLICATIONS

This application is a continuation application of U.S. patent application Ser. No. 17/013,004 filed on Sep. 4, 2020, now U.S. Pat. No. 11,453,894, which claims priority to U.S. Provisional Application Ser. No. 62/895,874, filed Sep. 4, 2019, the entire contents of which are incorporated herein by reference.

TECHNICAL FIELD OF THE INVENTION

The present invention relates in general to the field of cannabinoid and terpene preservation, including methods for the same.

STATEMENT OF FEDERALLY FUNDED RESEARCH

Not Applicable.

BACKGROUND OF THE INVENTION

Without limiting the scope of the invention, its background is described in connection with cannabidiolic acids.

One such process is taught in U.S. Pat. No. 9,908,832, issued to Leker, et al., entitled, "Decarboxylation of cannabidiolic acid in hemp biomass and hemp extract". This patent is said to teach decarboxylating carboxylic acids of cannabinoids in hemp extract or hemp biomass in which the hemp extract or hemp biomass is heated to a temperature of 40° C. to 100° degrees C. in the presence of one or more divalent or monovalent reagents.

What is needed are novel methods for cannabinoid and terpene preservation, including efficient, cost effective methods of production, and reducing waste.

SUMMARY OF THE INVENTION

In one embodiment, the present invention includes a method of preserving cannabinoid concentration in a biomass comprising: providing a hemp biomass in an aqueous solution; adding a culture of a cannabinoid preserving bacteria to the hemp biomass solution; and culturing the hemp biomass with the bacteria under conditions in which the cannabinoid concentration is maintained. In one aspect, the method further comprises the step of growing the bacteria to an exponential (log) grow phase prior to use. In another aspect, the method further comprises the step of culturing is performed at ambient temperature. In another aspect, the hemp biomass comprises dried flower and bud fraction without stalks and minimal stems. In another aspect, the hemp biomass comprises CBD-rich, low THC buds. In another aspect, the bacteria is selected from at least one of: *Lactobacillus cidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens*. In another aspect, the hemp biomass consists essentially of hemp flower. In another aspect, the hemp biomass is frozen prior to use. In another aspect, the method further comprises the step of culturing the hemp biomass is defined further as a fermentation step under air-tight conditions. In another aspect, the method further comprises the step of culturing is for 3, 4, 5, 6, 7, 10, 14, 18, 21, 25, 30, 35, 40, 45, 50, 55, or 60 days. In another aspect, the bacteria is cultured in MRS broth prior to adding to the hemp biomass solution. In another aspect, the hemp biomass is sterilized prior to use. In another aspect, the hemp biomass is *Cannabis sativa*.

In another embodiment, the present invention includes a method of preserving cannabinoid concentration in a biomass comprising: providing a hemp biomass in an aqueous solution; adding a culture of at least one of: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens* to the hemp biomass solution; and culturing the hemp biomass with the at least one of: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens* under conditions in which the cannabinoid concentration is maintained. In one aspect, the method further comprises the step of growing the at least one of: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens* to an exponential (log) grow phase prior to use. In another aspect, the step of culturing is performed at ambient temperature. In another aspect, the hemp biomass comprises dried flower and bud fraction without stalks and minimal stems. In another aspect, the hemp biomass comprises CBD-rich, low THC buds. In another aspect, the hemp biomass consists essentially of hemp flower. In another aspect, the hemp biomass is frozen prior to use. In another aspect, the step of culturing the hemp biomass is defined further as a fermentation step under air-tight conditions. In another aspect, the step of fermenting is for 3, 4, 5, 6, 7, 10, 14, 18, 21, 25, 30, 35, 40, 45, 50, 55, or 60 days. In another aspect, the at least one of: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens* is cultured in MRS broth prior to adding to the hemp biomass solution. In another aspect, the hemp biomass is sterilized prior to use. In another aspect, the hemp biomass is *Cannabis sativa*.

In one embodiment, the present invention includes a cannabinoid from a hemp plant preserved by the method comprising: providing a hemp biomass in an aqueous solution; growing a culture of bacteria selected from at least one of: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis;* or *Bacillus subtilis, B. amyloliquefaciens* into an exponential growth; adding a culture of a cannabinoid preserving bacteria to the hemp biomass solution; and culturing the hemp biomass with the bacteria under conditions in which the cannabinoid concentration is maintained.

BRIEF DESCRIPTION OF THE DRAWINGS

For a more complete understanding of the features and advantages of the present invention, reference is now made to the detailed description of the invention along with the accompanying figures and in which:

FIG. 1 shows the CBD preservation after 30 days at ambient summer temperatures.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "hemp biomass" refers to the portions of the Cannabis plants, e.g., Cannabis sativa, also known as Industrial hemp, that includes the dried cannabidiol (CBD) containing buds, which commonly includes the dried flower and bud fraction without stalks and minimal stems, which has the CBD-rich, low Tetrahydrocannabinol (THC) buds, which in some circumstances can also include the stalks. In one example the dried flower and bud fraction without stalks and minimal stems, has, <85% dried CBD-rich, low THC buds.

As used herein, the phrases "exponential growth phase" or "logarithmic growth phase" are used interchangeably to mean the condition in which a bacterial population undergoes exponential growth. The measurement of an exponential or logarithmic bacterial growth curve in batch culture typically requires bacterial cell counting by direct and individual (microscopic, flow cytometry), direct and bulk biomass, indirect and individual (colony counting), or indirect and bulk (most probable number, turbidity, nutrient uptake) methods.

As used herein, the term "culture conditions" refers to those culture conditions in which a bacterium grows and/or divides and is often, but not always, under temperature condition that optimize bacterial growth, such as above 4 degrees Celsius up to 45 degrees centigrade, but can also be 5, 6, 7, 8, 9, 10, 12, 15, 17, 20, 22.5, 25, 27.5, 30, 32.5, 35, 37.5, 38, 39, or 40 degrees Celsius. Often, the bacterium grows under air-tight conditions leading to fermentation of, in this case, a biomass. Generally, the culture conditions are kept for a period of time in which the biomass is partially fermented, such as, for 3, 4, 5, 6, 7, 10, 14, 18, 21, 25, 30, 35, 40, 45, 50, 55, or 60 days. Bacteria for use with the present invention include: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis*; and/or *Bacillus subtilis*.

Hemp harvest at the end of the growing season is bottle-necked in the drying and extraction process. Wet biomass loses significant amounts of high value cannabinoids and terpenes which impacts total yield per acre. Lower concentrations of cannabinoids in the biomass is more costly to extract because the extraction process is based on the biomass to solvent ratio.

The only proven technologies to preserve the cannabinoids in wet harvested hemp is to: (1) dry the product, or (2) freeze it to prevent degradation of the cannabinoids. Attempts to subject the harvest to nitrogen preservations resulted in significant losses and is not considered effective.

The use of naturally occurring bacteria for the preservation of the cannabinoid is novel. Typical biomass inoculants target the preservation of usable sugars and the suppression of harmful bacteria by lowering pH. While this product does lower pH, it is novel in its preservation of cannabinoids. It is also unexpected in that CBD and other cannabinoids are reported to have anti-microbial properties. Therefore, a live culture applied to this biomass is expected to be suppressed or killed by the hemp. Bacteria for use with the present invention include: *Lactobacillus acidophilus, L. casei, L. bifidum, L. plantarum, L. brevis, L. bulgaricus, L. fementum, L. helveticus,* or *L. rhamnosus; Bifdobacteruim lactis, B. longum, B. bifidum, B. breve, B. infantis*; and/or *Bacillus subtilis*.

Hemp farmers are paid for their harvest according to the CBD and cannabinoid concentration per unit of biomass. The value proposition is in the farmers favor by using the product compared to forgoing its use. The application of the product at the time of harvest via pump and sprayers is anticipated as the primary route to use. By applying the product on the harvest farmers reduce the risk of CBD degradation.

A pilot scale experiment was conducted using ~150 lbs of frozen hemp flower at 21 in Longmont, CO, where 3 different doses of the CBD extender was applied to ~15 Kg samples and sealed from oxygen. A 15 kg control sample was run as a comparator and all samples were held at ambient summer temperatures of 50 Degrees F. to >100 Degrees F. for one month.

The invention includes of a whole cell broth from a locally derived *Bacillus amyloliquefaciens* strain of bacteria. The whole cell broth was applied at various concentrations to partially frozen wet hemp flower. The samples were sealed in air-tight buckets and allowed to ferment over a 30 day period. At the end of 30 days, the buckets were opened and samples were sent to an independent laboratory for microbial and cannabinoid analysis. All samples to which the product was applied resulted in over two times the amount of cannabinoids as compared to the non-product control. Product applied samples also retained typical terpene odors associated with fresh hemp as compared to the control.

Materials: Whole Cell Broth—Colorado-derived *Bacillus amyloliquefaciens* (AC 1000 S strain) grown in De Man, Rogosa and Sharpe (MRS) media to approximately $1 \times 10^9$ CFU. MRS media is made as follows: dissolve 10 g Casein peptone, tryptic digest. 10 g Meat extract, 5 g Yeast extract, 20 g Glucose, 1 g TWEEN® 80, 2 g $K_2HPO_4$ in 850 ml of distilled water, adjust pH to between 6.2 and 6.5, bring to 1000 ml with distilled water, autoclave or filter sterilize. Hemp substrate—Wet mulched hemp flower grown in California. Received hemp from Hemp Extractors in a frozen state. The substrate was held at 0 to 1 degrees C. for 6 days prior to use. The hemp was partially frozen at the time of inoculation.

Equipment: 1 liter hand spray bottle, 2 liter graduated cylinder, Polypropylene tarp, 4×5 gallon polypropylene buckets and lids, Sledge hammer tamper, ethyl alcohol and rubber gloves.

Procedure:

(1) Tare 4×5 gallon buckets and lids (2) Pre-fill 4×5 gallon buckets with hemp flowers while tamping to compact with sledge hammer and record gross weights.

(3) Control Sample: Lay out polypro-tarp and mist with ethyl alcohol to sanitize surface. Allow approximately 3 minutes to dry and dump control bucket on surface to simulate the inoculation process. Using ethanol sanitized gloves mix the control to simulate the spray process. Hand-load the biomass in the tared bucket and tamp with sledgehammer to remove oxygen. Label and seal with lid.
(4) Use 4, 10, 15 gallon per sample: The procedure in step 3 was repeated using the equivalent of 4, 10 and 15 gallons whole cell broth per wet biomass ton by spray misting the product on the biomass and mixing prior to loading back into the 5 gallon buckets.

Results.

Data: The following application rates were applied:

| Sample | Net Biomass Kg | Whole Broth Applied ml |
|---|---|---|
| Control | 12.65 | 0 ml |
| 4 gallon/ton | 13.72 | 213 ml |
| 10 gallon/ton | 14.32 | 532 ml |
| 15 gallon/ton | 14.52 | 798 ml |

The samples were held under ambient summer conditions for July 2019. NOAA Data Longmont; Average 74.1 F, High 101 July 20. Low 55 July 10. Average daily temperature range 90 F to 59 F for 30 days.

FIG. 1 shows the CBD preservation after 30 days at ambient summer temperatures.

Surprisingly, it was found that using the present invention the application of the whole cell broth resulted in up to 2.5 times the amount of cannabinoids and CBD after holding at ambient temperatures for 30 days.

In one embodiment, the present invention includes a method of preserving cannabinoid concentration in a biomass consisting essentially of, or alternatively, consisting of: providing a hemp biomass in an aqueous solution; adding a culture of a cannabinoid preserving bacteria to the hemp biomass solution; and culturing the hemp biomass with the bacteria under conditions in which the cannabinoid concentration is maintained. In one aspect, the method further comprises the step of growing the bacteria to an exponential (log) grow phase prior to use. In another aspect, the method further comprises the step of culturing is performed at ambient temperature. In another aspect, the hemp biomass comprises dried flower and bud fraction without stalks and minimal stems. In another aspect, the hemp biomass comprises CBD-rich, low THC buds. In another aspect, the bacteria is selected from at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens*. In another aspect, the hemp biomass consists essentially of hemp flower. In another aspect, the hemp biomass is frozen prior to use. In another aspect, the method further comprises the step of culturing the hemp biomass is defined further as a fermentation step under air-tight conditions. In another aspect, the method further comprises the step of culturing is for 3, 4, 5, 6, 7, 10, 14, 18, 21, 25, 30, 35, 40, 45, 50, 55, or 60 days. In another aspect, the bacteria is cultured in MRS broth prior to adding to the hemp biomass solution. In another aspect, the hemp biomass is sterilized prior to use. In another aspect, the hemp biomass is *Cannabis sativa.*

In another embodiment, the present invention includes a method of preserving cannabinoid concentration in a biomass consisting essentially of, or alternatively, consisting of: providing a hemp biomass in an aqueous solution; adding a culture of at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens* to the hemp biomass solution; and culturing the hemp biomass with the at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens* under conditions in which the cannabinoid concentration is maintained. In one aspect, the method further comprises the step of growing the at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens* to an exponential (log) grow phase prior to use. In another aspect, the step of culturing is performed at ambient temperature. In another aspect, the hemp biomass comprises dried flower and bud fraction without stalks and minimal stems. In another aspect, the hemp biomass comprises CBD-rich, low THC buds. In another aspect, the hemp biomass consists essentially of hemp flower. In another aspect, the hemp biomass is frozen prior to use. In another aspect, the step of culturing the hemp biomass is defined further as a fermentation step under air-tight conditions. In another aspect, the step of fermenting is for 3, 4, 5, 6, 7, 10, 14, 18, 21, 25, 30, 35, 40, 45, 50, 55, or 60 days. In another aspect, the at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens* is cultured in MRS broth prior to adding to the hemp biomass solution. In another aspect, the hemp biomass is sterilized prior to use. In another aspect, the hemp biomass is *Cannabis sativa.*

In one embodiment, the present invention includes a cannabinoid from a hemp plant preserved by the method consisting essentially of, or alternatively, consisting of: providing a hemp biomass in an aqueous solution; growing a culture of bacteria selected from at least one of: *Lactobacillus acidophilus, L. casei, L. bifidum, L. plantarum, L. brevis, L. bulgaricus, L. fementum, L. helveticus*, or *L. rhamnosus; Bifdobacteruim lactis, B. longum, B. bifidum, B. breve, B. infantis*; or *Bacillus subtilis, B. amyloliquefaciens* into an exponential growth; adding a culture of a cannabinoid preserving bacteria to the hemp biomass solution; and culturing the hemp biomass with the bacteria under conditions in which the cannabinoid concentration is maintained.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A method of preserving a cannabinoid concentration from a hemp plant, comprising:
    culturing a *Cannabis sativa* biomass with a culture of bacteria selected from the group consisting of: *Lactobacillus acidophilus, Lactobacillus casei, Lactobacillus bifidum, Lactobacillus plantarum, Lactobacillus brevis, Lactobacillus bulgaricus, Lactobacillus fementum, Lactobacillus helveticus,* or *Lactobacillus rhamnosus; Bifidobacterium lactis, Bifidobacterium longum, Bifidobacterium bifidum, Bifidobacterium breve, Bifidobacterium infantis; Bacillus subtilis,* or *Bacillus amyloliquefaciens* under conditions in which the cannabinoid concentration is preserved, wherein the bacteria is grown to an exponential log growth phase prior to culturing with the *Cannabis sativa* biomass.

2. The method of claim 1, wherein the step of culturing is performed at ambient temperature.

3. The method of claim 1, wherein the *Cannabis sativa* biomass comprises dried flower and bud fraction without stalks and minimal stems; or the *Cannabis sativa* biomass comprises Cannabinoid-Rich (CBD-rich), low Tetrahydrocannabinol (THC) buds.

4. The method of claim 1, wherein the *Cannabis sativa* biomass consists essentially of *Cannabis sativa* flower.

5. The method of claim 1, wherein the *Cannabis sativa* biomass is frozen prior to use, is sterilized prior to culturing with the *Cannabis sativa* biomass, or both.

6. The method of claim 1, wherein culturing the *Cannabis sativa* biomass is fermented under air-tight conditions for 3, 4, 5, 6, 7, 10, 14, 18, 21, 25, 30, 35, 40, 45, 50, 55, or 60 days.

7. The method of claim 1, wherein the bacteria is cultured in a De Man, Rogosa and Sharpe (MRS) broth.

* * * * *